United States Patent [19]
Reinhard et al.

[11] Patent Number: 5,788,670
[45] Date of Patent: Aug. 4, 1998

[54] DUAL CHAMBER PREFILLABLE SYRINGE AND A METHOD FOR THE ASSEMBLY AND FILLING OF SAME

[75] Inventors: Michael Reinhard, Ober-Olm; Michael Spallek, Ingelham, both of Germany

[73] Assignee: Schott Glas, Mainz, Germany

[21] Appl. No.: 577,309

[22] Filed: Dec. 22, 1995

[30] Foreign Application Priority Data

Dec. 22, 1994 [DE] Germany .................. 44 45 969.6

[51] Int. Cl.$^6$ .................................. A61M 37/00
[52] U.S. Cl. ............................. 604/89; 604/191
[58] Field of Search ....................... 604/89, 90, 191

[56] References Cited

U.S. PATENT DOCUMENTS

| | | | |
|---|---|---|---|
| 4,613,326 | 9/1986 | Szwarc | 604/89 |
| 4,792,329 | 12/1988 | Schrender | 604/191 X |
| 5,607,400 | 3/1997 | Thibault et al. | 604/230 |
| 5,637,100 | 6/1997 | Sudo | 604/89 X |

FOREIGN PATENT DOCUMENTS

| | | |
|---|---|---|
| 0328699 | 8/1989 | European Pat. Off. . |
| 0520618A2 | 5/1992 | European Pat. Off. . |
| 0599649 | 6/1994 | European Pat. Off. . |
| 3816961 | 2/1989 | Germany . |
| 3736343 | 5/1989 | Germany . |
| 4204309 | 8/1992 | Germany . |
| 2010681 | 12/1977 | United Kingdom . |

OTHER PUBLICATIONS

H. Vetter, "Die Lyophilisierung von Arzneimitteln in Fertigspritzen" (1984), pp. 3–7.

Primary Examiner—Michael Buiz
Assistant Examiner—N. Kent Gring
Attorney, Agent, or Firm—Michael D. Bednarek; Kilpatrick Stockton LLP

[57] ABSTRACT

A fully assembled dual chamber prefillable syringe cylinder for the administration of two components having a syringe barrel which, in both its single cylinder and dual chamber cylinder embodiments, is connected to both a syringe head featuring a tip cap as well as to the finger grips and which is closed at its base by means of a moveable plunger with a plunger rod and into which an intermediate plunger is positioned with the intent of separating first and second chambers from each other and which features a bypass located in a first chamber, as well as to a method for the manufacture and filling of said fully assembled prefillable syringe.

12 Claims, 6 Drawing Sheets

5,788,670

DUAL CHAMBER PREFILLABLE SYRINGE AND A METHOD FOR THE ASSEMBLY AND FILLING OF SAME

BACKGROUND OF THE INVENTION

1. Field of the Invention

The invention refers to a prefillable syringe for medi and more specifically to a dual chamber prefillable syringe cylinder for the administration of two components having at the front end a syringe head and at the other end an open base, closed by means of a moveable plunger connected to a plunger rod and having an intermediate moveable plunger which separates first and second chambers from each other and having a bypass located in a top chamber.

Furthermore, the invention refers to a fully assembled dual chamber prefillable syringe for the administration of two components having a syringe barrel which, has a syringe head closed by a tip cap as well as a finger grips and which is closed at its base by means of a moveable plunger with a plunger rod and into which an intermediate moveable plunger is positioned with the intent of separating both chambers from each other and which features a bypass located in the top chamber, as well as to a method for the manufacture assembly, processing and filling of said fully assembled prefillable syringe.

2. Description of the Prior Art

Dual chamber prefillable syringes with barrels as described above are known from prior art: DE 37 36 343, DE 38 16 961, EP 0 599 649 A1, EP 0 328 699, DE 42 04 309 A1, and are described in an article by H. Vetter "Die Lyophilisiering von Arzneimitteln in Fertigspritzen" ("Lyophilization of Substances in Prefillable Syringes") in: *Die Pharmazeutische Industrie*, Vol. 46 (1984), No. 10, pp. 1045–1049.

In the medical field, dual chamber prefillable syringes are commonly used for the injection of substances consisting of two components, each stored initially in the first and second chambers of the syringe respectively. There are two possibilities for mixing the components, i.e., a liquid/liquid combination or a solid/liquid combination.

The advantage of the dual chamber prefillable syringe lies in the fact that the mixing process of the two components is accomplished without necessitating the transfer of the components into another container, and that the subsequent injection occurs directly from the original container. Currently, the following practice is still in wide use: by means of an empty disposable syringe, water or another diluent is extracted from a vial or container and subsequently transferred into another vial or container containing a powder where the latter is dissolved. By means of the same syringe, the resulting solution is removed and only then the syringe is ready for injection. These multiple steps are complex and time-consuming. Furthermore, there are risks associated with the procedures, such as contamination and mix-up errors in handling the substances often resulting from the disposable syringes not being labeled permanently for substance identification.

By contrast, the use of dual chamber syringes is easier. During storage, the intermediate plunger is located on that side of the bypass that faces away from the syringe head. When, for purposes of injection, the plunger rod connected to the plunger is moved forward, all the while utilizing the finger grips for support, both plunger rod and plunger as well as the intermediate plunger are moved into the direction of the syringe head. Simultaneously, a ventilation process at the syringe head takes place. Once the intermediate plunger has reached the bypass, the liquid component from the first chamber streams past it into the second chamber, whereupon the two components from the respective first and second chambers are mixed and subsequently injected.

The dual chamber prefillable syringe known from prior art and described above consists of a single syringe barrel made of glass or polymer materials. The single barrel contains both chambers. Hence, both components are transferred into a single cylinder divided into two chambers by a simple plunger.

This type of design poses the disadvantage and latent risk of cross-contamination of the two components if some minor amount of one component enters into the other's chamber during processing potentially posing a serious medical hazard. The incorporation of both chambers within a single cylinder also poses obstacles during lyophilization. During lyophilization, the entire, relatively long, syringe barrel is placed into the freeze drying equipment, the operation of which is extremely complex. It is not a functional imperative that the part of the syringe cylinder constituting the second chamber be placed into the freeze drying equipment. This results in a significant under-utilization of the space in the freeze drying chamber with immense cost implications regarding efficiency and productivity, major factors in mass production.

SUMMARY OF THE INVENTION

It is an object of the invention to provide a costeffective manufacture of a dual chamber syringe which allows separate filling processes of two components to prevent cross contamination of the same and which allows an optimal utilization of the processing chamber of the freeze drying equipment in such cases where one of the components requires freeze-drying.

A further object of the invention is to achieve a cost-effective method for avoiding cross contamination during the manufacture and filling of the dual chamber syringe.

The means for attaining the object of the invention lies in a special embodiment of the syringe barrel which differs from the syringe barrel known from the prior art and described above in that the invention provides a cylinder consisting of two detachable barrels which are connected to each other at their respective front ends to form a single syringe cylinder, having a first detached barrel, with the syringe head, which constitutes the first chamber of the syringe cylinder. This first barrel contains the bypass and is sealed by an intermediate plunger at the opposite end of the syringe head. The syringe cylinder also comprises a second detached barrel which constitutes the second chamber and with the finger grips.

Based on the fully assembled prefillable syringe, the means for attaining the object of the invention lies in the syringe cylinder which, according to the invention, consists of two separate barrels, whereby the first barrel, with the syringe head, constitutes the first chamber within which is contained a bypass, and which is sealed by an intermediate plunger located at the opposite end of the syringe head; and whereby the second barrel, with the finger grips, constitutes the second chamber, and which is sealed by the plunger. Syringe head and finger grip may be individual part connected to the respective barrel or be integral parts of the respective barrels.

With respect to the method for manufacturing and filling the fully assembled prefillable syringe, the means for attaining the object of the invention are attained by the initial production of the two detached barrels of the syringe cylinder. Subsequently, the detached barrels are filled separately, only the front end detached barrel is sent through the freeze drying equipment, if applicable, and sealed. Following these procedures, the two detached barrels ultimately are connected to each other.

The syringe cylinder of the dual chamber syringe, according to the invention, is the result of adjoining two barrels, which allows for the separate filling of the two chambers. This eliminates the risk of cross contamination almost entirely. The filling process will be explained in further detail below.

If one of the two components requires lyophilization, only the barrel containing that liquid to be lyophilized is placed in the freeze drying equipment, thereby greatly enhancing the productivity of the freeze-drying process.

Typically, a closed syringe head is an integral part of the barrel or is a separate part connected to the syringe barrel, i.e., the first detached barrel. In its fully assembled state, the first detached barrel's opposite end is sealed with the intermediate plunger after the filling of the first component. Hence, the first detached barrel is sealed to form a closed container. By contrast, the second detached barrel is, in the initial phase of assembly, closed by the plunger at only one end. This means, that the second detached barrel is not a closed system until both detached barrels have been connected to each other.

This embodiment of the invention provides for the syringe to be engineered in a way that the second detached barrel is sealed along the connecting plane by means of an auxiliary movable plunger, thus allowing for both containers to be filled and sealed completely independently of each other and to be attached to each other to form an overall closed system. This procedure allows for more latitude in the filling and assembly of the syringe. By way of example, a ready-to-use syringe may be composed of the first detached barrel at the syringe head containing a freeze-dried component and the second detached barrel containing a diluent. The second barrel is connected to the finger grips and its chamber is enclosed by the plunger and auxiliary movable plunger. As an added advantage, the process described above also meets the general requirement of terminal sterilization, e.g. autoclaving at 121° C. for all diluents contained in dual chamber syringes.

Further advantages may be achieved if, by way of improving the invention, the two detached barrels of dual chamber syringes are made of polymer materials. The production of polymer materials is inexpensive; and plastics have few impurities and are easy to sterilize. The concomitant method provides for the manufacture of the detached barrels by way of injection molding under clean-room conditions and for their packaging in hermetically sealed containers. In addition, it provides for the separate filling, lyophilization, if applicable, and sealing of the individual barrels. Not until these processes are completed are the detached barrels joined together.

In another variation of the invention's embodiment, one detached barrel consists of glass and the other of polymer materials. An advantage of this embodiment is the capability to chose the syringe barrels' material directly in accordance with their specific requirements. By way of example, the detached barrel facing the syringe head could be made of glass if it holds a freeze-dried component. Glass has excellent barrier properties which minimize water vapor diffusion. The other detached barrel intended for holding the solvent water could be made of a suitable plastic material.

Currently, water used for medical purposes is stored in vials made of plastic materials like polypropylene, polyethuphene, polycarbonate, etc.

A further variation of the invention's embodiment has both detached barrels being made of glass. This is usually the case when the barrier properties of the containers are an essential requirement.

The barrier properties of plastic detached barrels can be improved if, in accordance with the embodiment of the invention, the plastic detached barrels are barrier coated either on the inside or outside. Metal, ceramic or vitreous coatings like Al, Au or $Sio_2$ are available for such purposes. Another possibility is to manufacture the detached barrels using two or more different plastic resins and coinjection molding resulting in a layer structure of the walls. Also an additional metal, ceramic or vitreous coating may be placed between the plastic layers.

In general, preference is given to a single material using no coatings. For example, cyclo-defin-copolymers (COC) produced by Hoeshst Gerugny under the trademark TOPAS or by DAICYO, Japan under the trademark of CZ-resin are well suited because of the excellent barrier properties regarding water vapor permeability.

The advantages of the embodiment described above are such that, even in cases of a container's high barrier properties, resins may be used. The plastic material itself is the substance used for molding the syringe barrels while the coating provides for the barrier function.

There are several options to chose from when it comes to adjoining the two detached barrels. They include welding, bonding and form-fitting snaps. The suitability of the various options basically depends on the materials used for the syringe barrels. If both detached barrels are made of synthetic materials, welding is a suitable option; however, bonding is just as appropriate, especially in such cases where the detached barrels both are made of glass. A further embodiment of the invention provides for the adjoining of the two cylinder parts by means of a snap seal irrespective of whether they are made of glass or synthetics.

After the injection of the syringe contents, the plunger position is beyond the front barrel's bypass, thus, rendering the syringe cylinder's back end "open" and, depending on the syringe's position, leading to some backflow of the liquid in the bypass. To avoid such an occurrence, the embodiment of the prefillable syringe, according to the invention, is engineered to feature a retaining disc positioned on the plunger rod with a diameter equal to the syringe cylinder's internal diameter. During injection, the retaining disc enters the syringe cylinder upon the plunger moving into the bypass area.

There are several options available for engineering the embodiment of the bypass. The most common version currently contemplated is a protrusion of the syringe cylinder.

However, protrusions do not allow for packaging syringe cylinders with high density, e.g. body to body, one cylinder touching the other. For the same reason, syringe cylinders (made of glass) are not usually moved through a sterilization tunnel body to body, rather, they are placed in an additional containment designed especially for this purpose.

The disadvantage resulting from the protrusion embodiment can be avoided if the first detached barrel is made of plastic materials and features grooves on its inside walls. The bypass is formed by the grooves which run in axial direction.

It is, hence, the embodiment of the bypass grooves within the inner walls that allow for an ideally dense packing of syringe cylinders. The grooves also constitute a reduction in the thickness of the cylinder's wall.

BRIEF DESCRIPTION OF THE DRAWINGS

The present invention will become more clearly appreciated as the disclosure of the present invention is made with reference to the accompanying drawings wherein.

DETAILED DESCRIPTION OF THE PREFERRED EMBODIMENTS

Figure 1:
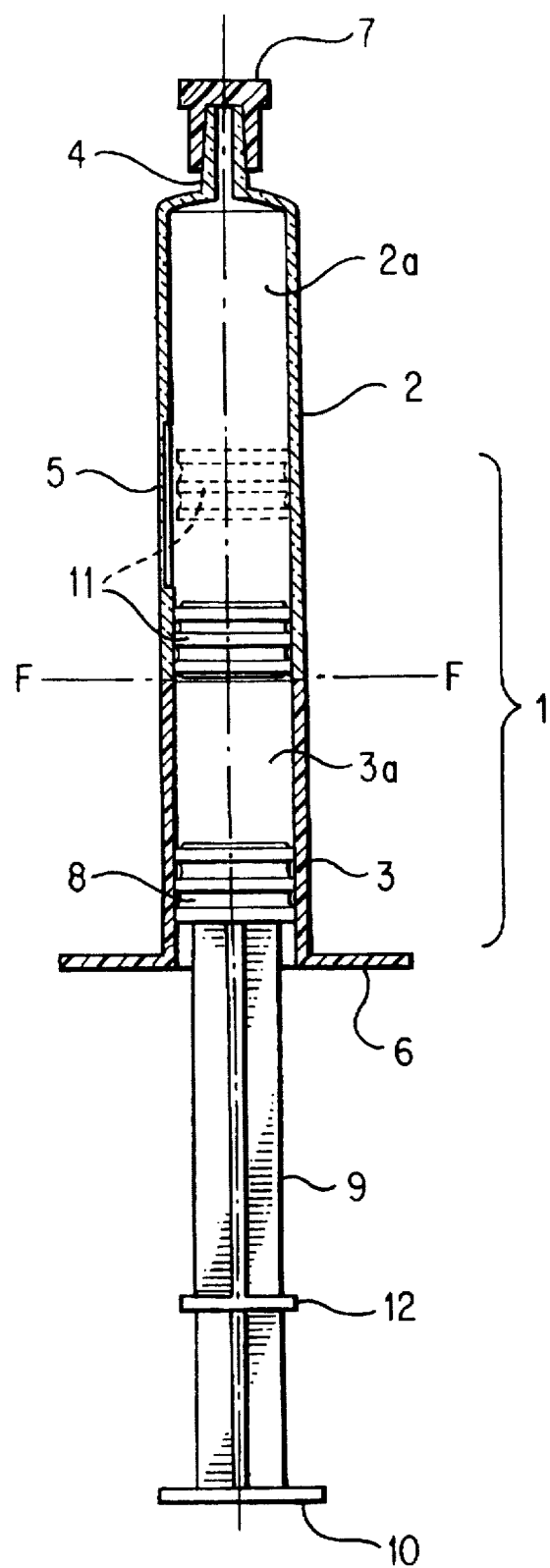
FIG. 1 illustrates a cross-section of a dual chamber prefillable syringe having a syringe cylinder consisting of the two detached barrels, according to the invention.

In a cross-sectional view, FIG. 1 illustrates the basic structure of the prefillable syringe, according to the invention, for the injection of two components. This could involve two liquids or a solid (freeze-dried component or powder) and a liquid (solvent).

The dual chamber prefillable syringe features a syringe cylinder 1, according to the invention, consisting of two detached barrels 2 and 3 which are adjoined along the F—F plane (connecting plane), i.e., vertically to the syringe barrel's longitudinal axis. Each barrel 2 and 3 encloses a chamber 2a and 3a.

A syringe head 4 is an integral part of the detached barrel 2. Furthermore, the top barrel 2 features a bypass channel 5, in this case in the form of a protrusion. Standard finger grips 6 are on the base of the syringe cylinder, i.e., on the detached barrel 3. An alternative design provides for an embodiment whereby the finger grips 6 are placed or clipped onto the outside or into the inside of the base of the barrel as a separate part, depending on the material used for the detached barrel 3. Such embodiments are generally well known in the prior art.

The syringe body consists of the syringe cylinder 1 with the syringe head 4 and the finger grips 6. The syringe head 4 is closed by a standard tip cap 7. At the finger grips 6, a plunger 8 is located; it moves within the syringe cylinder 1 by means of a plunger rod 9 having a thumb support 10. The two chambers 2a and 3a are separated from each other by means of a moveable intermediate plunger 11. The intermediate plunger 11 is situated at the rear of the top barrel 2 and serves as a seal between the first chamber 2a and the second chamber 3a along the connecting plane F—F.

A retaining disc 12 with a diameter equal to the syringe cylinder's interior diameter is fitted to the plunger rod 9. In some cases, it is positioned in order to enter the syringe cylinder during plunger movement when the plunger reaches the bypass 5. Without the retaining disc, the rear part of the syringe cylinder would virtually be "open" in such circumstances causing residual liquid in the by-pass-channel to escape, depending on the syringe's position. The presence of the retaining disc 12 prevents any liquid from flowing out of the syringe's back end.

In the embodiment of FIG. 1, a tip cap 7 is positioned on the syringe head 4. Prior to injection, the tip cap 7 is removed and replaced by a needle.

In some embodiments, the needle is directly fixed in the syringe head. One such embodiment comprises the first top barrel 2 being made of polymer materials with a needle fixed by injection insert-injection molding, e.g., molding around the needle during the injection molding of the band 2. An alternative common practice involves the bonding of the needle into the syringe head. As a result of the various fitting options, the term "prefillable syringe" also refers to the container alone without the bonded or inserted needle.

Standard procedures apply for the administration of an injection using the fully assembled dual chamber prefilled syringe as illustrated in FIG. 1. Initially, manual pressure is applied to the plunger rod's 9 thumb support 10 and to the finger grips 6, thereby setting the plunger 8 in motion in the direction of the syringe head. Simultaneously, ventilation is occurring at the syringe head. This causes the intermediate plunger 11 to move in the same direction; the connection between the two chambers 2a and 3a is opened once the plunger has reached the bypass 5, which is indicated by the shaded areas in the illustration. As soon as the intermediate plunger has been activated as just described, the component contained in chamber 3a, typically a liquid, flows past the intermediate plunger initiating a reaction with the component contained in chamber 2a. For instance, if chamber 2a contains a freeze-dried component and chamber 3a contains water for injection as the solvent, the freeze-dried component is dissolved in the activated position of the intermediate plunger—and the syringe is ready for injection.

The two-part syringe cylinder offers many key benefits with respect to the assembly and filling of syringes which were already illustrated in the introduction. This will be demonstrated below in further detail using FIGS. 2 and 3.

Figure 2A:
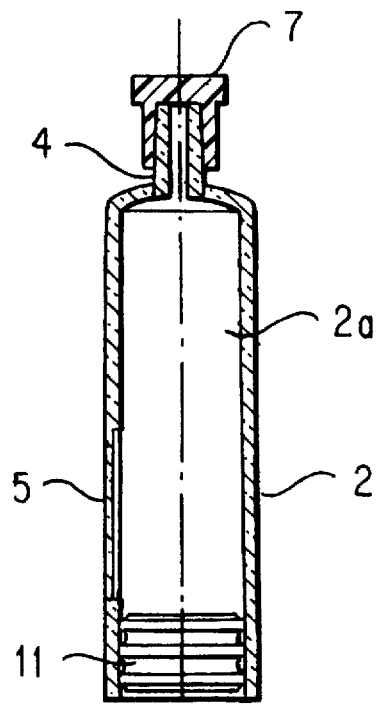
FIG. 2A illustrates an enlargement of a detached barrel of the syringe cylinder, according to FIG. 1, and its assembly.
Figure 2B:
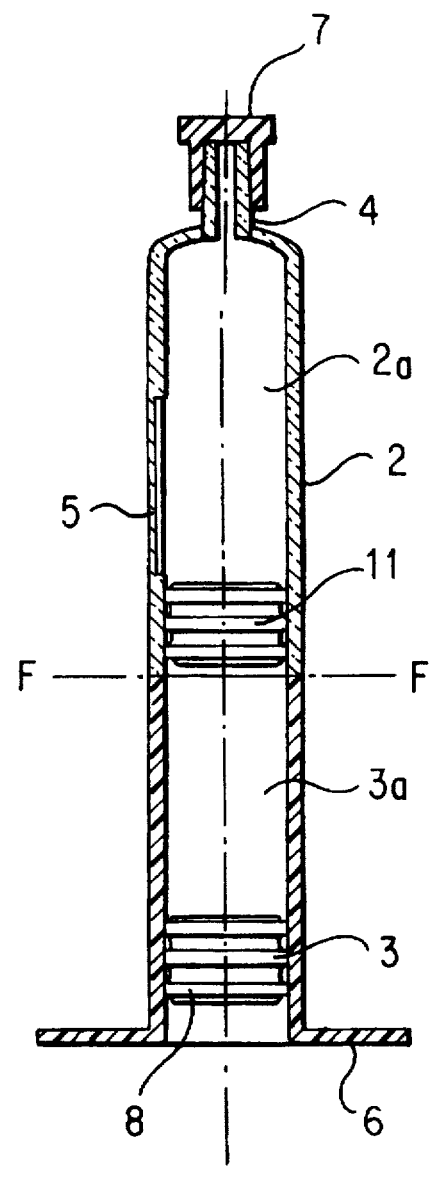
FIG. 2B illustrates an assembly of the components of FIG. 2A.

FIG. 2A illustrates the two unattached barrels 2 and 3 of syringe cylinder 1 as depicted in FIG. 1. FIG. 2B illustrates the two barrels—as in FIG. 1—after they have been affixed to each other along the connecting plane F—F.

It is readily apparent from FIG. 2 that the dual chamber syringe, according to the invention, allows for filling the two chambers separately from each other, thereby virtually eliminating the risk of cross contamination during filing. Should one of the chambers require specialized treatment during the filling process, such as lyophilization, then only the barrel in question, not the entire syringe cylinder, will undergo such special treatment. Thus, the productivity of the manufacturing process is greatly enhanced, particularly if the process involves complex treatment devices which require tight stacking or if its economical operation is highly dependent on the efficient utilization of the treatment space. The lyophilizator, for example, is one such apparatus.

As illustrated in FIG. 2A, the top of the detached barrel 2 is closed off by a syringe head 4 covered with a tip cap 7. After a component has been filled into the chamber 2a, the barrel's base is secured with an intermediate plunger 11.

Now the barrel 2 constitutes a completely sealed container. Detached barrel 3 is closed off by the plunger 8 at its base. This allows for the filling of the barrel through the open, upper end. As indicated by the arrows, the detached barrel 2 is fitted onto the barrel 3 along the connecting plane F—F. This results in the complete syringe as illustrated in FIG. 2B.

FIG. 2 clearly demonstrates that there are various methods for filling and affixing the barrels. One example would be to attach barrel 3 without the plunger to the hermetically sealed barrel 2, then turn it over, as shown in FIG. 2A, fill it and, finally, seal it with the plunger 8. Similarly, it is possible to fill the barrel 2, separately or affixed to barrel 3, at the syringe head 4 provided the embodiment of the syringe head allows for such a procedure. Another option is to combine the procedures described above when connecting the barrels to each other. The decision as to what constitutes the best suitable procedure depends on the materials used for the syringe parts, the method of assembly, and/or the components to be transferred into the barrels.

Figure 3A:
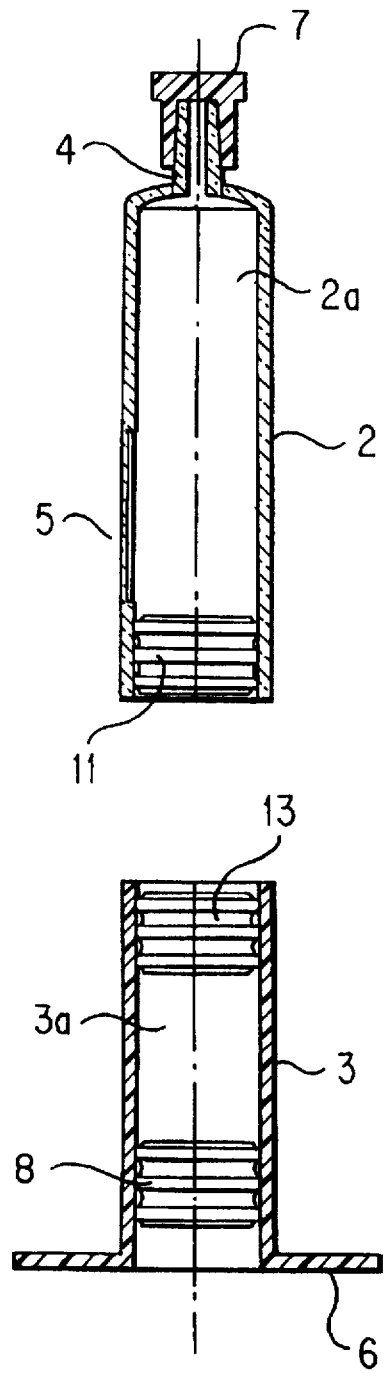
FIG. 3 (consisting of FIGS. 3A and 3B) illustrates a variation on the embodiment of the detached barrel, analogous to FIG. 2.
Figure 3B:
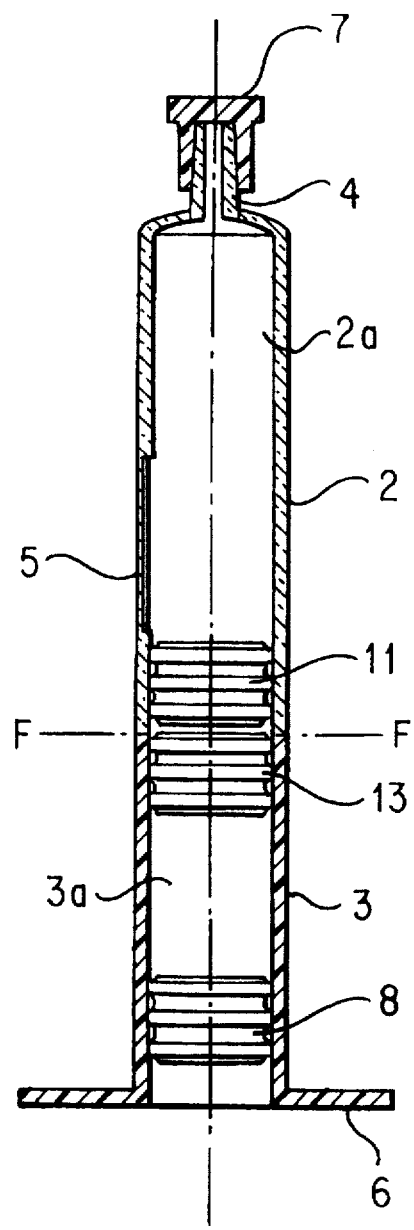

FIG. 3 illustrates another embodiment of the syringe, according to the invention as depicted in FIG. 1, constituting an enlarged version of FIG. 2. Components common to both figures are referenced by identical reference numerals. In the embodiment depicted in FIG. 3, the end of the barrel 3 facing the connecting plane F—F and still open in FIGS. 1 and 2, is now, upon completion of the filling procedure, closed off by means of an auxiliary moveable plunger 13. This embodiment allows for the separate filling and closure of both barrels as seen in FIG. 3A and for the subsequent attachment of the resulting two hermetically sealed containers to each other to form the syringe as seen in FIG. 3B.

The filling procedures for the two barrels can be done from both ends and in a variety of ways, as illustrated in FIG. 2.

The means for attaining the object of the invention is best illustrated in FIG. 3. This embodiment allows for a greater degree of flexibility with respect to the filling and assembly of the syringe. For example, the completely sealed chamber 2a may contain a pre-mixed, separately freeze-dried substance, while the completely sealed chamber 3a may contain a solvent. This procedure facilitates the terminal sterilization of the solvent for the dual chamber syringe.

As set forth in the introduction, both cylinders may be made of glass or resin materials. Another option is to make one out of glass and the other out of plastic.

A front barrel 2 made of resin allows for the advantageous embodiment of the bypass 5. Instead of providing a bypass in the shape of a protrusion, as illustrated in FIGS. 1–3, this embodiment provides for a bypass without increasing the cylinder's diameter. It is impossible to package syringe cylinders with protrusions most densly, e.g., body to body. Furthermore, the syringes must be placed into special devices during processing. These protrusions often result in the syringes being incompatible with simple standard processing like transporting by pushing syringe cylinders having body to body contact. Such problems are overcome by means of the bypass embodiment as shown in FIG. 4.

Figure 4A:
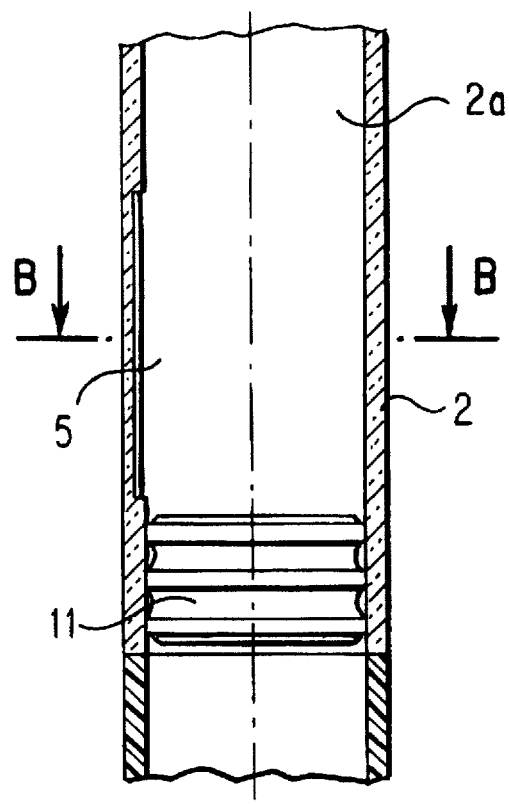
FIG. 4 (consisting of FIGS. 4A and 4B) illustrates an embodiment of the bypass in the front barrel having grooves in the cylinder wall.
Figure 4B:
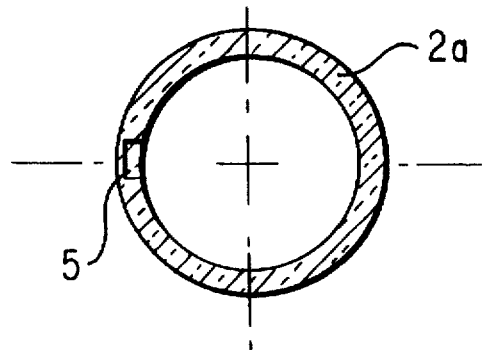

FIG. 4A depicts a partial longitudinal section through the front barrel 2 with the inserted intermediate plunger 11. FIG. 4B shows a segment along the line B–B of FIG. 4A. Along the bypass section, the internal wall is provided with at least one axial groove, notch or recess, etc. which forms the bypass 5.

Figure 5A:
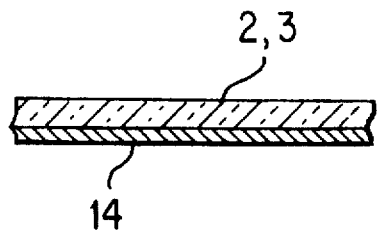
FIG. 5A illustrates an alternative for coating plastic barrels.
Figure 5B:
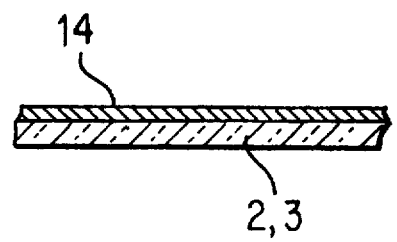
FIG. 5B illustrates a second alternative for coating plastic barrels.

As mentioned in the introduction, the use of plastic barrels which have been coated on the inside or outside are preferable due to the resulting enhancement of the barrels' minimization of evaporation. This coating is illustrated once more in a diagram in FIG. 5. The walls of the individual plastic barrels 2 and/or 3 feature a coat 14 on the inside, as seen in FIG. 5A, or on the outside, as seen in FIG. 5B. Alternatively, a coat 14 may be applied to both the inside and outside walls of the respective barrels 2 and 3. The coat may be made of metallic, ceramic or vitreous material.

There is an array of possibilities available to the skilled artisan for connecting the barrels 2 and 3 from which the most suitable is chosen depending on the existing conditions and circumstances. FIGS. 6–9 illustrate typical methods for adjoining the two cylinders.

Figure 6:
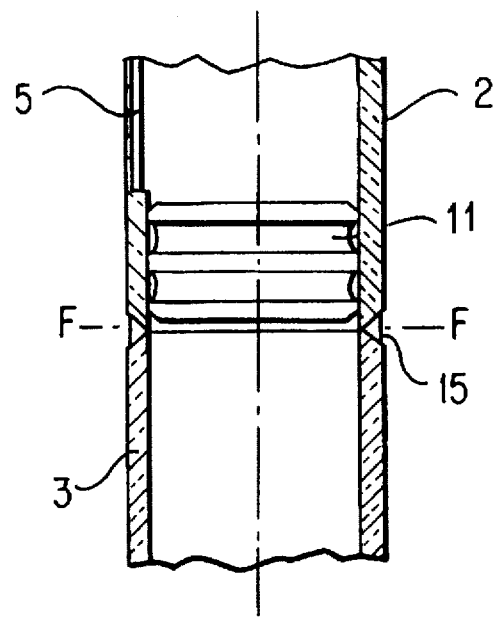
FIG. 6 illustrates the adjoining of the two detached barrels by means of bonding, with an adhesive.

FIG. 6 depicts an embodiment whereby the two cylinders 2 and 3 are bonded together along the connecting plane F—F. The front connecting sides of both cylinders are bezeled for purposes of creating a bonding groove 15. The bonding method is especially suitable for cylinders consisting of either glass or plastic materials.

Figure 7:
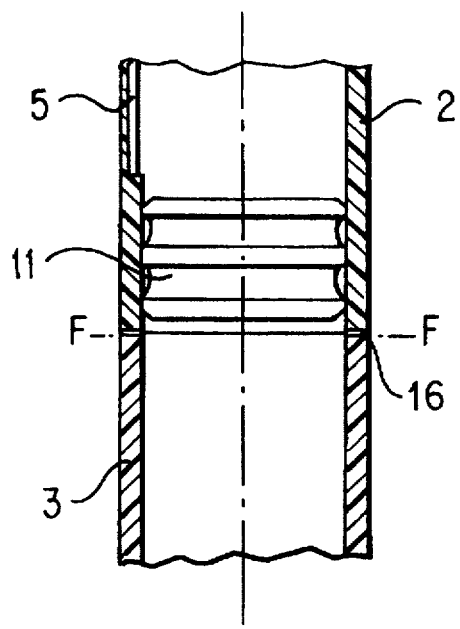
FIG. 7 illustrates the adjoining by means of welding.

FIG. 7 depicts an embodiment whereby the two cylinders 2 and 3 are adjoined to each other by a welding seam 16 along the connecting plane F—F. The welding method is especially suitable for barrels consisting each of synthetic materials.

Two embodiments for the sealing method of the syringe head are illustrated in FIGS. 8 and 9. The two options are especially useful when the front chamber 2a has been filled with a freeze-dried component because it is essential that a connection to the outside environment is created during lyophilization to enable vapors to escape.

Figure 8A:
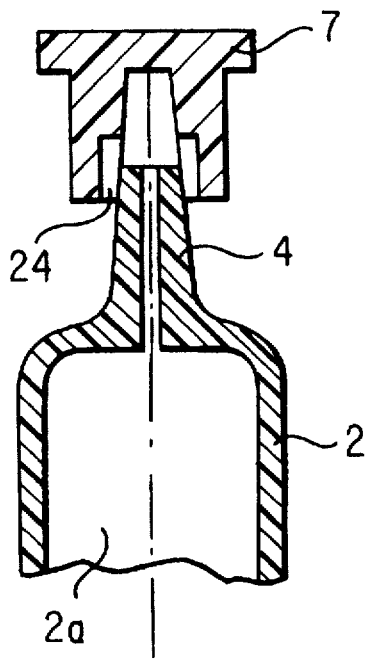
FIG. 8 (consisting of FIGS. 8A and 8B) illustrates a first embodiment of the syringe head.

FIG. 8 gives an enlarged view of the tapered syringe head 4 with the tip cap 7. The tip cap features axial recesses 24 which allow for a connection between the chamber 2a of the front barrel 2 with the outside environment, as illustrated in FIG. 8A, depicting a tip cap 7 not completely fitted to seal off the chamber 2a.

Figure 8B:
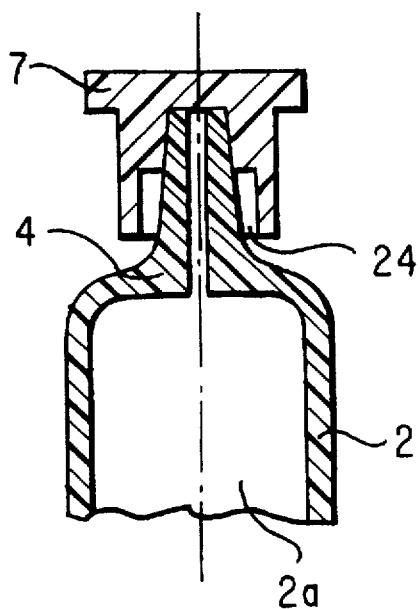

FIG. 8B depicts the tip cap 7 as completely fitted for a tight seal of the pre-mixed freeze-dried component inside the chamber 2a.

Figure 9A:
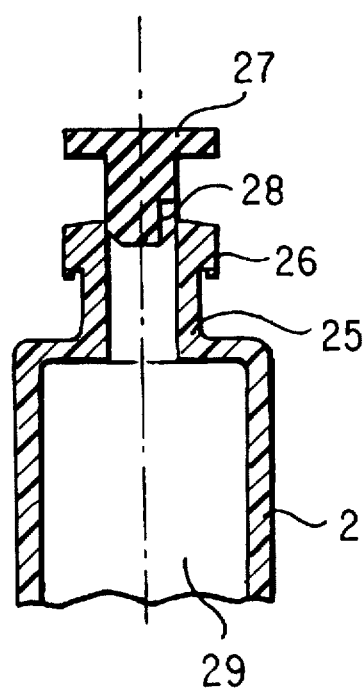
FIG. 9 (consisting of FIGS. 9A and 9B) illustrates a second embodiment of the syringe head.

In the embodiment shown in FIG. 9, the syringe cylinder, i.e., the front cylinder 2, has a cartridge-type opening 25 which features an essentially cylindrical interior outline and an external collar 26. Into the opening, a stopper 27 is fitted. The stopper 27 is made of elastic material with sealant properties like pharmaceutical rubber. FIG. 9A depicts the version where the stopper has not been fitted for an entirely tight seal, thereby creating a connection between the external environment and the interior of the syringe in order to allow freeze-drying of the content.

Figure 9B:
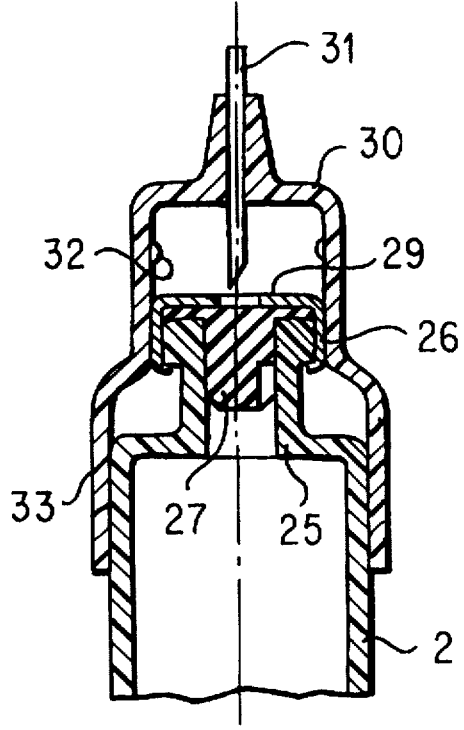

In FIG. 9B, the stopper has been inserted into the opening completely. It is crimped by an aluminum cap 29, thereby sealing off the freeze-dried component entirely. A needle hub 30 is placed upon the syringe head into which the injection needle 31 is fitted. The needle hub features two guide segments 32 and 33. Segment 32 and the external collar have the same diameter as segment 33 and the detached cylinder 2. The segments are designed to help guide the needle hub onto the syringe cylinder, while the needle 31 pierces the stopper 27 and thus renders the syringe ready for injection.

The preferred method for the assembly and filling of the prefillable syringes is summarized as follows. Initially, the two detached barrels of the syringe are manufactured; if necessary, the inner wall is coated with a layer of silicone oil, etc. to assure proper gliding of the plungers; subsequently the barrels' respective chambers are filled, subjected to lyophilization, if applicable, and sealed. Finally, once the two previous steps have been completed, the two cylinders are attached to each other.

Special advantages in the production process result when both barrels are made of plastic materials, i.e., manufactured by means of injection molding under clean-room conditions, sterilized in hermetically sealed containers, subsequently filled separately, subjected to lyophilization, if applicable, and sealed. If necessary, a gliding layer of silicone oil, silicone emulsion, etc. is applied prior to sterilization. Once all of these steps have been completed, the two cylinders are attached to each other.

The aforementioned production process eliminates costly washing procedures and allows for easy sterilization by means of gamma radiation or, alternatively, ethylene oxide gas. Production processes in which modern synthetics are utilized, such as cyclic olefin copolymer (COC), yield glassy, transparent syringe cylinders possessing excellent physical properties.

What is claimed is:

1. A dual chamber prefillable syringe for the administration of two medical components, comprising:

a syringe cylinder (1) comprising a first cylinder piece (2) having two ends and a second cylinder piece (3) having two ends, the first cylinder piece and the second cylinder piece being joined together at respective ends thereof without expanding the diameter at the connecting plane (F), whereby:

the first cylinder piece encloses a first chamber and the second cylinder piece encloses a second chamber, the first cylinder piece (2) being connected at one end thereof with a syringe head (4) and the first cylinder piece further comprising axially extending bypass grooves (5) recessed on the inner wall and being closed at the other end with an undivided movable intermediate plunger (11) over the complete length thereof, the second cylinder piece (3) being closed at one end by means of a movable injection plunger (8) with a plunger rod (9) fittable into it and the second cylinder piece further comprising at this end a finger grip (6) which is fitted as a separate piece to said second cylinder piece.

2. A prefillable syringe, as in claim wherein the second cylinder piece can be sealed off at its end facing toward the connecting plane (F) by means of an additional moveable auxiliary plunger.

3. A prefillable syringe, as in claim 1, wherein said first and second cylinder pieces are made of resin materials.

4. A prefillable syringe, as in claim 1, wherein one of said first and second cylinder pieces is made of glass, while the other is made of synthetic materials.

5. A prefillable syringe, as in claim 4, wherein at least one of the synthetic cylinder pieces includes an inside or outside barrier coating.

6. A prefillable syringe, as in claim 1, wherein each of said first and second cylinder pieces are made of glass.

7. A prefillable syringe, as in claim 1, wherein both first and second cylinder pieces are adjoined to each other by means of welding.

8. A method for the manufacture and filling a dual chamber prefillable syringe for the administration of two medical components, comprising the following steps:

manufacturing first and second cylinder pieces of the syringe cylinder;

filling the chamber of each cylinder piece separately with a corresponding medical component;

subjecting the first cylinder piece to lyophilization, if applicable;

sealing the chamber of each cylinder piece separately; and joining the two cylinder pieces together to form the complete syringe cylinder.

9. A method as in claim 8, wherein both cylinder pieces are produced by means of injection molding under clean-room conditions and are subsequently sterilized in a hermetically sealed container for filling and sealing.

10. A prefillable syringe, as in claim 1, wherein said first and second cylinder pieces are connected to each other by means of bonding.

11. A prefillable syringe, as in claim 1, wherein the cylinder pieces include front connecting sides that are bezeled for purposes of creating a bonding groove.

12. A prefillable syringe, as in claim 1, comprising a retaining disc that is affixed to the plunger rod, and wherein the disc's diameter is equal to the syringe cylinder's interior diameter, such that the retaining disc is immersed into the syringe cylinder when the plunger moves into the bypass area.

* * * * *